(12) United States Patent  
Kortenbach et al.

(10) Patent No.: US 6,551,315 B2  
(45) Date of Patent: Apr. 22, 2003

(54) METHODS AND APPARATUS FOR THE TREATMENT OF GASTRIC ULCERS

(75) Inventors: Juergen A. Kortenbach, Miami Springs, FL (US); Michael Sean McBrayer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 128 days.

(21) Appl. No.: 09/730,911

(22) Filed: Dec. 6, 2000

(65) Prior Publication Data

US 2002/0068935 A1 Jun. 6, 2002

(51) Int. Cl.⁷ ............................................. A61B 18/18
(52) U.S. Cl. ............................ 606/46; 606/52; 606/207
(58) Field of Search ........................... 606/46, 51, 52, 606/205, 206, 207; 600/562, 563, 564, 565, 566, 567

(56) References Cited

U.S. PATENT DOCUMENTS

| | | |
|---|---|---|
| 1,750,874 A | 3/1930 | Campbell |
| 2,377,540 A | 5/1945 | Costa ........................ 128/309 |
| 3,921,641 A | 11/1975 | Hulka ........................ 128/321 |
| 4,735,194 A | 4/1988 | Stiegmann ..................... 128/6 |
| 4,825,259 A | 4/1989 | Berry, Jr. ..................... 356/241 |
| 5,336,222 A | 8/1994 | Durgin, Jr. et al. ........... 606/50 |
| 5,373,854 A | 12/1994 | Kolozsi ....................... 128/749 |
| 5,482,054 A * | 1/1996 | Slater et al. ............... 606/46 X |
| 5,496,310 A | 3/1996 | Exconde et al. ............. 606/205 |
| 5,501,698 A | 3/1996 | Roth et al. ................. 606/205 |
| 5,507,797 A | 4/1996 | Suzuki et al. ............... 606/140 |
| 5,562,694 A * | 10/1996 | Sauer et al. ............. 606/205 X |
| 5,575,806 A | 11/1996 | Nakao et al. ............... 606/207 |
| 5,582,617 A * | 12/1996 | Klieman et al. ......... 606/205 X |
| 5,662,588 A | 9/1997 | Iida ............................ 600/121 |
| 5,674,220 A | 10/1997 | Fox et al. .................... 606/51 |
| 5,707,344 A | 1/1998 | Nakazawa et al. .......... 600/127 |
| 5,722,421 A * | 3/1998 | Francese et al. ........ 606/205 X |
| 5,800,449 A | 9/1998 | Wales ........................ 606/172 |
| 5,820,630 A | 10/1998 | Lind .......................... 606/208 |
| 5,891,162 A | 4/1999 | Sugarbaker et al. ........ 606/207 |
| 5,897,507 A * | 4/1999 | Kortenbach et al. .... 606/205 X |
| 5,906,630 A * | 5/1999 | Anderhub et al. ...... 606/205 X |
| 5,968,056 A | 10/1999 | Chu et al. ................... 606/140 |
| 6,001,110 A | 12/1999 | Adams ........................ 606/151 |
| 6,013,095 A | 1/2000 | Ouchi ......................... 606/205 |
| 6,110,127 A | 8/2000 | Suzuki ........................ 600/565 |

* cited by examiner

*Primary Examiner*—Edward K. Look  
*Assistant Examiner*—Richard A. Edgar  
(74) *Attorney, Agent, or Firm*—David P. Gordon; David S. Jacobson; Thomas A. Gallagher

(57) ABSTRACT

A surgical tool attaches to the distal end of an endoscope and provides a rotatable treating element. According to one embodiment of the invention, the treating element is a pair of jaws provided with cautery capability. According to an aspect of the invention, the treating element is capable of multiple movements from a first closed position, to an open position, to a second closed position and back to the first closed position via a single controller with a single linear movement.

27 Claims, 4 Drawing Sheets

METHODS AND APPARATUS FOR THE TREATMENT OF GASTRIC ULCERS

BACKGROUND OF THE INVENTION

1. Field of the Invention

The invention relates to surgical instruments and methods. More particularly, the invention relates to methods and apparatus for the minimally invasive treatment of gastric ulcers using a cautery device, although it is not limited thereto.

2. State of the Art

Minimally invasive (also known as endoscopic) surgery is not a new technology. However, it is only in recent years that such surgery has become so widely accepted that it is used in many diverse procedures. Minimally invasive surgery typically involves the making of a small incision (5–10 mm) in the vicinity of the surgical site, the installation of a port through the incision, and the extension of an endoscope through the port to the surgical site. Alternatively, an endoscope is sometimes lubricated and inserted through a body cavity such as the rectum or esophagus.

Gastrointestinal bleeding is a somewhat common and serious condition that can be fatal if left untreated. This problem has prompted the development of a number of endoscopic therapeutic approaches to achieve hemostasis, such as the injection of sclerosing agents, the attachment of mechanical hemostatic devices and contact electrocautery techniques. Mechanical hemostatic devices are typically in the form of clamps, clips, staples, sutures, etc. which are able to apply sufficient constrictive forces to blood vessels so as to limit or interrupt blood flow. Such devices are disclosed in U.S. Pat. No. 6,001,110. Electrocautery techniques involve the use of either monopolar or bipolar electrodes which are contacted to ulcerous tissue. A well known electrocautery device is disclosed in U.S. Pat. No. 5,336,222.

The known clip techniques and cautery techniques are only adequate for relatively small ulcers because the clips and/or cautery probes must be delivered through the working lumen of an endoscope. In addition to optical elements which carry fiber optics to illuminate the surgical site and which deliver an image from the surgical site, the endoscope typically has two or three lumena: one or two lumen(a) for aspiration and irrigation, and one (the working lumen) through which a surgical tool may be passed. The working lumen is typically very small in size (e.g., about 3 mm in diameter), and thus the size of the tools which may be used with a typical endoscope are severely limited in size.

Bleeding gastric ulcer lesions are not limited in size and are frequently too large to be effectively treated with the known mechanical and electrical techniques.

SUMMARY OF THE INVENTION

It is therefore an object of the invention to provide methods and apparatus for the minimally invasive treatment of gastric ulcers.

It is also an object of the invention to provide methods and apparatus for the minimally invasive treatment of gastric ulcers using a cautery device.

It is another object of the invention to provide methods and apparatus for the minimally invasive treatment of gastric ulcers using a cautery device which is capable of treating relatively large lesions.

It is a further object of the invention to provide methods and apparatus for the minimally invasive treatment of gastric ulcers using a cautery device which is usable in conjunction with existing endoscopes.

In accord with these objects which will be discussed in detail below, the apparatus of the present invention includes a flexible coil having a proximal end and a distal end (as used herein proximal end means the end closest to the practitioner and distal end means the end closest to the surgical site) with a pull wire extending therethrough. An actuation device is coupled to the proximal ends of the coil and the pull wire for reciprocally moving one of the pull wire and the coil relative to the other. A pair of jaws are coupled to the distal ends of the coil and pull wire such that relative movement of the coil and pull wire causes opening and closing of the jaws. The jaws are rotatably coupled to a clevis means which is adapted to be coupled to the distal end of an endoscope. According to the invention, at least one jaw has an "open" structure, with a rim but substantially no jaw cup. The jaws are U-shaped, semi-circular, or horse shoe shaped and are provided with a cautery capability by selectively coupling the coil, the pull wire, or both to a source of cauterizing energy.

According to one of the methods of the invention, the clevis is attached to the distal end of an endoscope and the distal end of the endoscope is delivered to the surgical site with the aid of the optics of the endoscope and with the jaws of the invention closed by activation of the actuation device. A grasper (used herein to denote any instrument such as a forceps, biopsy forceps, snare, suction device or other instrument for mechanically or otherwise grabbing, gripping, or retaining tissue) is inserted through the working lumen of the endoscope. The jaws of the apparatus of the invention are then opened so that the grasper is extended between the opened jaws (typically through the open structure of at least one jaw) to grasp the ulcerous tissue. The grasping instrument is withdrawn to pull the ulcerous tissue between the opened jaws. When the tissue is in place, the jaws of the present invention are closed and the cauterizing energy is activated to cauterize the ulcerous tissue and thereby hemostasis. The procedure may be repeated for treatment of other ulcerous tissue in the vicinity before the apparatus is withdrawn with the endoscope.

According to the presently preferred embodiment, one of the jaws of the cautery device is coupled to the coil and the other is coupled to the pull wire, whereas both jaws are coupled to the clevis. This arrangement permits the jaws to assume two different closed positions: a first closed position wherein both jaws extend substantially parallel and adjacent to the face of the distal end of the endoscope and a second closed position where both jaws extend substantially perpendicular to the face of the distal end of the endoscope. The first closed position is preferred when moving the endoscope to and from the surgical site, and because the jaws have an open structure, the jaws do not block the optical "vision" of the endoscope.

According to a further preferred aspect of the invention, the clevis is provided with upper and lower stops and the coil and pull wire are coupled to the jaws in such a way that different moment arms result. This permits the jaws to be moved from the first closed position to an open position, to the second closed position, and back to the first closed position with a single actuation device having a single linear movement.

According to still another preferred aspect of the invention, the jaws are insulated from each other at their pivotal connection to the clevis so that they may be provided with bipolar cautery capability via separate connections to the coil and pull wire which are also insulated from each other.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
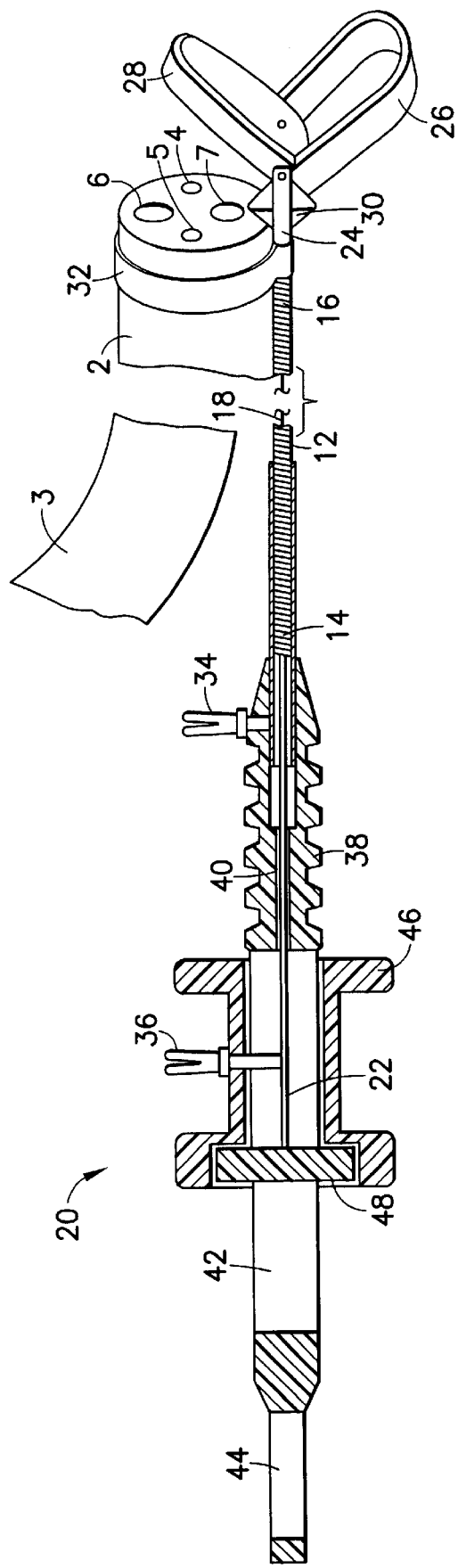
FIG. 1 is a schematic broken side elevation view in partial section and partial perspective of a first embodiment of the apparatus of the invention.

Turning now to FIG. 1, an apparatus 10 according to a first embodiment of the invention includes a flexible coil 12 having a proximal end 14 and a distal end 16 with a pull wire 18 extending therethrough. An actuation device 20, described in more detail below, is coupled to the proximal end 14 of the coil and the proximal end 22 of the pull wire for reciprocally moving one of the pull wire and the coil relative to the other. A clevis 24 is coupled to the distal end 16 of the coil 12 and a pair of jaws 26, 28 are rotatably coupled to the clevis. The jaws 26, 28 are also coupled to the distal end 30 of the pull wire 18 such that movement of one of the pull wire or the coil relative to the other causes the jaws to open or close. According to one aspect of the invention, the clevis 24 is provided with an upstanding ring 32 which is adapted to attach to the distal end 2 of a conventional endoscope 3 having optical elements 4 and 5 which carry fiber optics for illumination and a lens and fiber optics for capturing an image, an irrigation/aspiration lumen 6, and a lumen 7 which constitutes a hollow working channel for receiving an instrument. According to another aspect of the invention, the jaws 26, 28 are substantially larger than the working channel 7 so as to be able to cauterize relatively large ulcers.

According to a preferred embodiment, the coil 12 or the pull wire 18, or both are provided with an electrical coupling 34, 36, respectively for coupling to a source of cautery current. Those skilled in the art will appreciate that when two electrical couplings are provided, the pull wire 18 will be provided with insulation so that it does not electrically contact the coil 12. Alternatively, two electrically insulated pull wires may be mechanically coupled to the spool, but electrically coupled to different poles. It will also be appreciated that in either bipolar configuration, the jaws 26, 28 will be electrically insulated from each other. Certain techniques for providing electrical bipolar couplings are disclosed, e.g., in U.S. Pat. No. 5,395,369 to McBrayer et al., the complete disclosure of which is hereby incorporated herein by reference.

The actuation device 20 is substantially the same as used in many conventional endoscopic biopsy forceps. It includes a shaft 38 having a distal throughbore 40, a slot 42 in communication with the throughbore 40 and a proximal thumb ring 44. A spool 46 having a cross member 48 is disposed over the slot 42. The proximal end 14 of the coil 12 is coupled to the shaft 38 and the proximal end 22 of the pull wire 18 is coupled to the cross member 48 of the spool.

According to another aspect of the invention, the jaws 26, 28 are "open" shapes (e.g. U-shaped, semi-circular, horse shoe shaped). That is, the jaws are defined by a rim but substantially no jaw cup. Thus, the jaws do not obstruct with the optical elements or lumena 4–7 at the distal end 2 of the endoscope 3.

Figure 2:
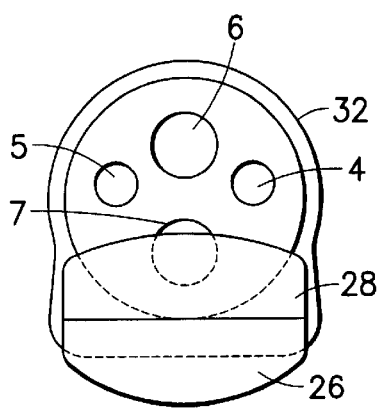
FIG. 2 is a schematic distal end view of the apparatus of FIG. 1 with the jaws closed.
Figure 3:
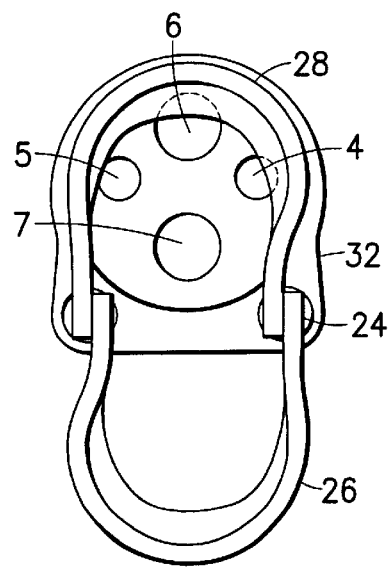
FIG. 3 is a view similar to FIG. 2 with the jaws opened.
Figure 4:
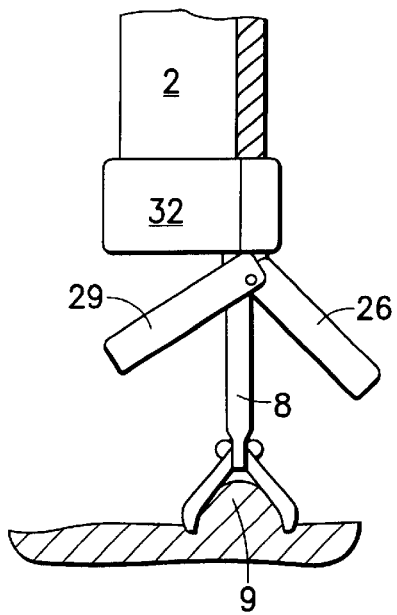
FIG. 4 is a schematic broken side elevation view of the apparatus of FIG. 1 with the jaws opened and a grasper extended from the endoscope grasping ulcerous tissue.
Figure 5:
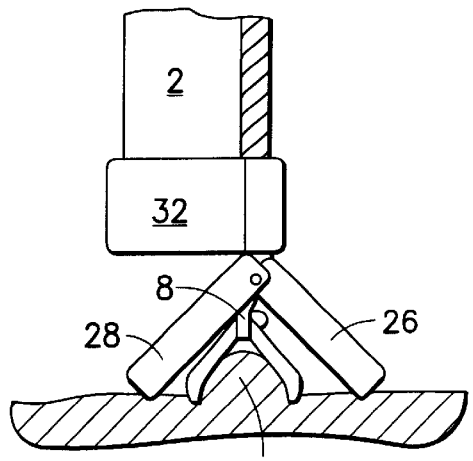
FIG. 5 is a view similar to FIG. 4 with the grasped tissue drawn into the jaws.
Figure 6:
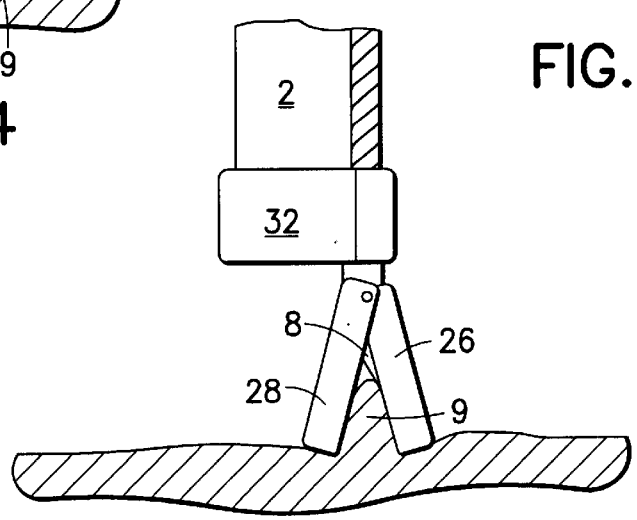
FIG. 6 is a view similar to FIG. 5 with the jaws closed around the tissue.

Turning now to FIGS. 2–6, according to one of the methods of the invention, after the clevis has been attached to the distal end of the endoscope, the jaws 26, 28 are closed as shown in FIG. 2 by activation of the actuation device 20. In the closed position, the optical elements 4, 5 of the endoscope are not obstructed by the jaws 26, 28. After the endoscope is delivered to the surgical site with the aid of the optical lumina, the jaws 26, 28 are opened as shown in FIG. 3. In the opened position shown in FIG. 3, neither the optical elements nor the lumina (including the working channel 7) of the endoscope are obstructed. As shown in FIG. 4, with the jaws open, a grasping instrument 8 such as a forceps, a biopsy forceps, a snare, a suction device, etc., is extended through the working channel 7, through an opening in the jaw 28 and/or into a space between the opened jaws 26, 28. The grasper is then actuated to grasp or retain the tissue 9 (e.g., by actuating jaws or suction), and the grasper is then partially withdrawn and/or the distal end of the endoscope is moved closer to the tissue as shown in FIG. 5 to pull the tissue between the opened jaws 26, 28. Once the tissue is between the jaws of the bipolar apparatus 10, the jaws are closed as shown in FIG. 6. According to one aspect of the invention, cauterizing energy is delivered to the jaws 26, 28 when the jaws are in the position shown in FIG. 6 to cauterize the tissue therebetween. The procedure may be repeated for treatment of other tissue in the vicinity before the apparatus is withdrawn with the endoscope.

Figure 7:
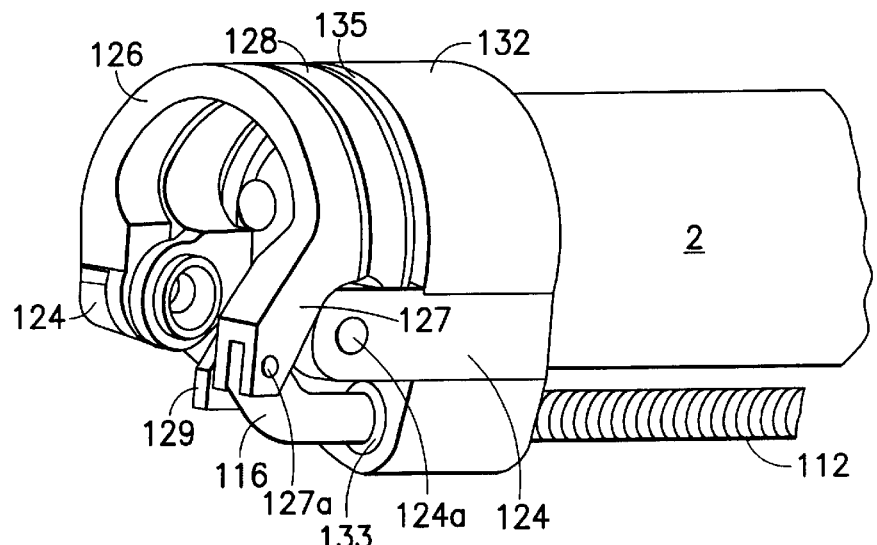
FIG. 7 is a schematic broken perspective view of a presently preferred embodiment of the jaw assembly of the invention with the jaws in a first closed position.
Figure 8:
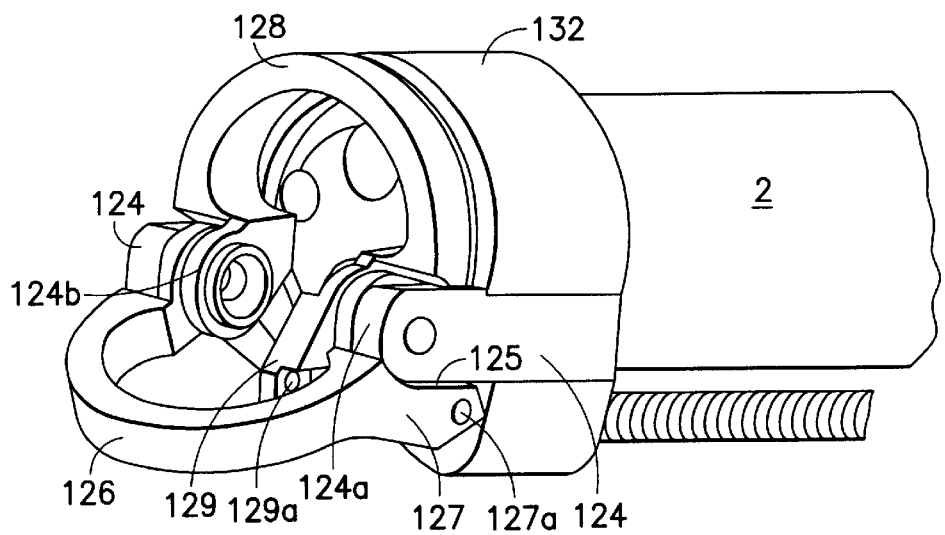
FIG. 8 is a view similar to FIG. 7 with the jaws in an opened position.
Figure 9:
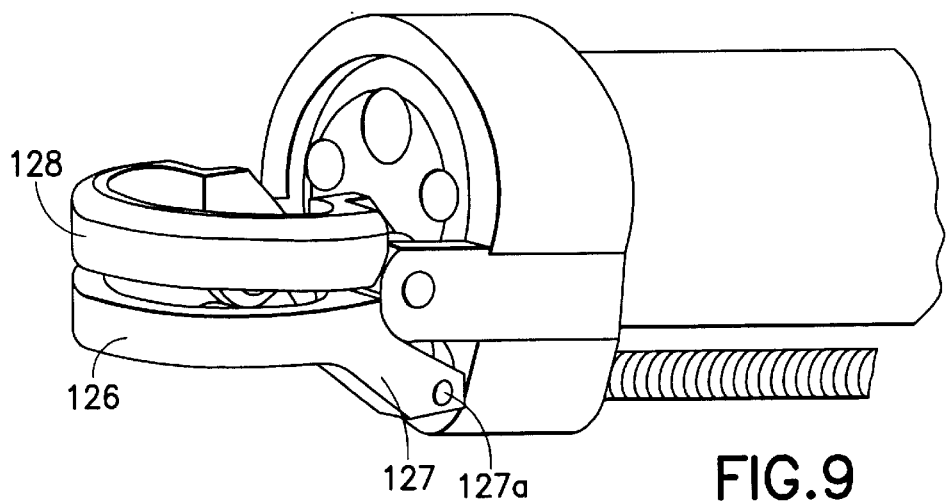
FIG. 9 is a view similar to FIG. 8 with the jaws in the second closed position.
Figure 7A:
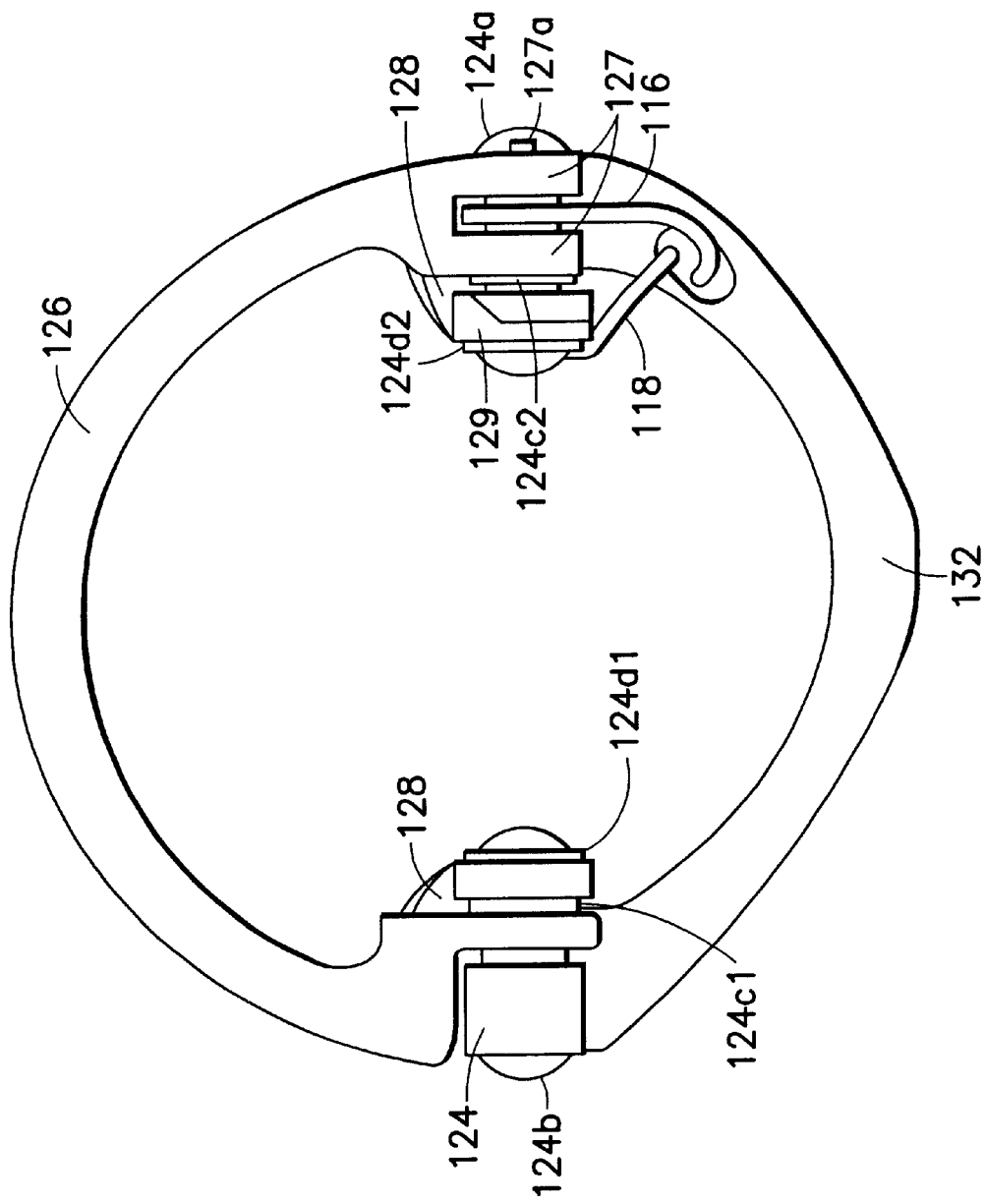
FIG. 7a is a schematic distal end view of the presently preferred embodiment with the jaws in the closed position.

Referring now to FIGS. 7, 7a, 8, and 9, a second embodiment of the invention is disclosed which is substantially similar to the first embodiment but for the configuration of the clevis and the jaws (i.e., the proximal actuation mechanism is as shown in FIG. 1). In this embodiment, the clevis means 124 includes an upper ring portion 132 for coupling to the distal end 2 of an endoscope. The upper portion 132 may have an inner diameter which is substantially the same size as the outer diameter of the endoscope and cemented, press fit, or otherwise affixed to the distal end of the endoscope. Alternatively, the upper ring portion may be sized to slide over the distal end of the endoscope. The clevis means 124 also includes a lower side throughbore 133 which is dimensioned to allow the distal end of the coil to move therethrough. Jaws 126, 128 are rotatably coupled to pivot pins 124a, 124b of the clevis 124. The jaws are preferably substantially semi-circular in shape as shown and are electrically isolated from each other by insulating washers 124c1, 124c2, 124d1, 124d2. It should be mentioned that the clevis element, including the upper ring is preferably non-conductive. The distal jaw 126 is provided with a rotator arm 127 to which the distal end of the coil is coupled at pivot pin 127a. The coil 112 actually has a rigid extension 116 at its distal end with a side opening which allows the pull wire 118 to make a 90° turn proximally of the distal end of the coil extension. The distal end of the rigid extension is coupled to the pivot pin 127a. The proximal jaw 128 is provided with a rotator arm 129 to which the distal end of the pull wire 118 is coupled at hole 129a. FIG. 7 illustrates the jaws in a first closed position. FIG. 8 shows the jaws in an open position. FIG. 9 shows the jaws in a second closed position. As shown in the Figures, the clevis means 124 is provided with a stop 125 which engages the moment arm 127 when the jaws are in the open position shown in FIG. 8 and prevents further forward movement of the jaw 126. Similarly, the upper ring 132 has a distal face 135 which prevents backward movement of the jaw 128 beyond the position shown in FIGS. 7 and 8. According to this embodiment of the invention, the distance between the pivot pin 127a and the pivot pin 124a is slightly longer than the distance between the hole 129a and the pivot pin 124a, giving the rotator arm 127 a longer moment than the rotator arm 129.

As mentioned above, the jaws 126, 128 are coupled via the coil and pull wire respectively to an actuator such as the actuation device 20 in FIG. 1. It should be intuitively clear that when the spool 46 of the actuator 20, which is attached to the pull wire, is moved distally, the distal end of the pull wire moves distally relative to the distal end of the coil. However, because movement of the pull wire cannot effect rotation of the jaw 28 as it is stopped against the face of the ring 132, the coil is effectively pulled in the proximal direction relative to the clevis means 124, thereby causing the jaw 126 to rotate about the pins 124a, 124b which constitutes the rotation axis for both jaws. This results in the jaws assuming the position shown in FIG. 8 where the rotator arms 127 and 129 are as far apart as they can be because further movement of the jaws 126, 128 is limited by the stop 125 and the distal face 135. When the spool is moved proximally, it urges proximal movement of the pull wire and distal movement of the coil. From the position of the jaws shown in FIG. 8, proximal movement of the spool will move the pull wire proximally causing the jaw 128 to move toward the jaw 126. Jaw 126, on the other hand, will only move slightly because it is impeded by the tissue it is grabbing. Thus, when the spool is moved proximally, the jaws will assume the position shown in FIG. 9 with the tissue (not shown) therebetween for cauterization. Further proximal movement of the spool would have no effect on the jaws but for the longer moment of rotator arm 127 as compared to rotator arm 129. Further proximal movement of the spool urges further proximal movement of the pull wire. However, because the pull wire is now in a most proximal position, stopped by the jaws being closed, a relative proximal movement is effected only by distal movement of the coil relative to the clevis means. The longer moment arm of the jaw 126, makes the distal movement of the coil possible. This additional movement of the coil causes the jaws to rotate about the pivots and move from the position shown in FIG. 9 to the initial closed position shown in FIG. 7. In the closed position in FIG. 7, the jaws are substantially perpendicular to the longitudinal axis of the endoscope and do not substantially block the optics or the working channel of the endoscope.

As with the first embodiment, it will be appreciated that cautery current is applied to one or both of the end effectors (jaws 126, 128) via the pull wire and/or coil. Where bipolar cautery is desired, the end effectors are preferably electrically insulated relative to each other, and each end effector is provided with a different pole.

According to another aspect of the invention, bipolar cauterization of the surgical site may be achieved by providing the grasping device which extends through the endoscope with one pole, and by providing one or both jaws of the external tool with a second electrical pole.

It will be appreciated that the disclosed invention provides several inventive aspects. It is believed that the aspect of providing a rotatable treating member at the distal end of an endoscope without passing through a lumen of the endoscope is inventive. It is also believed that providing a cautery treatment element at the distal end of an endoscope without passing through a lumen of the endoscope is inventive. It is further believed that it is inventive to provide an arrangement of jaws (or other end effectors such as graspers, dissectors, scissors, clip appliers, staplers, etc.) and a single actuation means whereby the single actuation means can move the jaws from a first closed position to an open position and to a second closed position which is displaced from the first closed position. It is believed to be additionally inventive to provide such an arrangement whereby the single actuation means can then move the jaws back to the first closed position. It is believed that it is inventive to provide a pair of jaws at the distal end of an endoscope which are relatively large but which do not interfere with the operation of the endoscope when the jaws are opened or closed. It is believed that it is an inventive surgical procedure to pass a grasper through a pair of open jaws of a surgical tool, grasp tissue with the grasper, pull the tissue with the grasper between the open jaws and then close the jaws on the tissue. It is believed that it is inventive to provide a grasper which extends through an endoscope with a first electrical pole, and a tool external the endoscope with a second electrical pole for conducting a bipolar cautery procedure on tissue.

There have been described and illustrated herein several embodiments of a surgical instrument for use with an endoscope. While particular embodiments of the invention have been described, it is not intended that the invention be limited thereto, as it is intended that the invention be as broad in scope as the art will allow and that the specification be read likewise. Thus, while the illustrative embodiments incorporate most or all of the inventive features of the invention, it will be appreciated as described above that some of the inventive features may be applied alone or in combinations other than those of the disclosed embodiments. In addition, it will be appreciated that while particular embodiments have been shown, other embodiments of the invention can be utilized. For example, rather than providing a tool adjacent and clipped to the endoscope which utilizes a coil and a pull wire, the coil could be replaced with a tube (e.g., a hypotube), and/or the pull wire could be replaced with a rod, or a cable (metallic or otherwise). In each case, the extent of flexibility of tube and rod can be dependent upon the application in which the endoscope is used. Also, rather than providing a tool where the jaws rotate about pivot pins or axis, one jaw could be caused to rotate, pivot, or otherwise open relative to the other jaw, e.g., using an arcuate coupling such as disclosed in U.S. Pat. No. 5,389,104 to Hahnen et al., which is hereby incorporated by reference herein in its entirety. For purposes herein, all such rotation or pivoting is called "rotation". It will therefore be appreciated by those skilled in the art that yet other modifications could be made to the provided invention without deviating from its spirit and scope as so claimed.

What is claimed is:

1. A surgical tool for use with an endoscope having a distal end and at least one lumen, comprising:

a) a clevis means for coupling to the distal end of the endoscope without passing through the lumen of the endoscope;
b) a first rotatable member rotatably coupled to said clevis means;
c) a second rotatable member rotatably coupled to said clevis means;
d) a pulling element having a proximal end and a distal end, said distal end of said pulling element being coupled to said first rotatable member by a first moment arm;
e) a coil or tube having a proximal end and a distal end, said pulling element extending through said coil or tube, said distal end of said coil or tube being coupled to said second rotatable member by a second moment arm; and
f) an actuator coupled to said proximal end of said pulling element and said coil, wherein
one of said first and second moment arms is longer than the other.

2. A surgical tool according to claim 1, further comprising:
g) coupling means coupled to said pulling element for coupling said pulling element to a source of cauterizing energy.

3. A surgical tool according to claim 1, wherein:
said first and second rotatable members are a pair of opposed jaws.

4. A surgical tool according to claim 1, wherein:
said clevis means is provided with a first stop which limits movement of said first rotatable member and a second stop which limits movement of said second rotatable member.

5. A surgical tool according to claim 1, further comprising
g) first electrical coupling means coupled to said pulling element for coupling said pulling element to a first pole of a source of cauterizing current; and
h) second electrical coupling means coupled to said coil or tube for coupling said coil or tube to a second pole of the source of cauterizing current.

6. A surgical tool according to claim 1, further comprising:
g) electrical means coupled to at least one of said pulling element and said coil or tube for providing said at least one of said pulling element and said coil or tube with a source of cauterizing current.

7. A surgical tool for use with an endoscope having a distal end and at least one lumen, comprising:
a) a clevis means for coupling to the distal end of the endoscope without passing through the lumen of the endoscope;
b) a pair of jaws coupled to said clevis means;
c) an actuator coupled to at least one of said jaws for rotating it relative to the other of said jaws from an open position to a closed position; and
d) cautery coupling means for coupling at least one of said jaws to a source of cauterizing energy, wherein
said jaws are configured such that when they are in the open position, a tool passing through the working channel of the endoscope can pass through the open jaws.

8. A surgical tool according to claim 7, wherein:
said cautery coupling means includes means for coupling one pole of a cautery current source to one jaw and the other pole of the cautery current source to the other jaw.

9. A surgical tool according to claim 7, where the endoscope has an optical element and wherein:
said jaws are configured such that they do not interfere with the optical element of the endoscope.

10. A surgical tool according to claim 7, wherein:
said actuator is coupled to both of said jaws, and
said jaws are movable from a first closed position to an open position and from the open position to a second closed position which is displaced from said first closed position.

11. A surgical tool, comprising:
a) a clevis;
b) a pair of end effectors rotatably coupled to said clevis;
c) a single actuation means coupled to said end effectors for rotating said end effectors relative to said clevis, wherein
said end effectors are jaws, at least one of which is defined by a rim with substantially no jaw cup, said rim being defined by a curve lying in a plane which transects the axis of said actuation means.

12. A surgical tool according to claim 11, wherein:
actuation of said single actuation means rotates said end effectors from a first closed position to an open position and to a second closed position, said second closed position being angularly displaced from said first closed position.

13. A surgical tool according to claim 12, wherein:
said first and second closed positions are angularly displaced by approximately ninety degrees.

14. A surgical tool according to claim 13 or use in conjunction with an endoscope, further comprising:
d) coupling means for coupling said clevis to the distal end of the endoscope.

15. A surgical tool according to claim 14, where the endoscope has at least one optical element and wherein:
when said jaws are in said first closed position, they do not interfere with the at least one optical element of the endoscope.

16. A surgical tool according to claim 15, where the endoscope has a working channel and wherein:
when said jaws are in said open position they do not interfere with the working channel of the endoscope.

17. A surgical tool for use with an endoscope having at least one optical element and at least one working lumen, comprising:
a) a clevis means for coupling to the distal end of the endoscope without passing through the lumen of the endoscope;
b) a pair of open jaws coupled to said clevis means; and
c) actuation means coupled to at least one of said open jaws for rotating it relative to the other of said open jaws from an open to a closed position, wherein
said open jaws are configured such that when said open jaws are in the open position, neither the optical lumen nor the working lumen is obstructed by either jaw, wherein:
said pair of jaws are too large to pass through the lumen of the endoscope when in said closed position.

18. A surgical tool according to claim 17, wherein:
said pair of jaws have a diameter similar to a diameter of a front face of the endoscope.

19. A surgical tool according to claim 17, wherein:
when said jaws are in said open position, an instrument passing through the working lumen of the endoscope is free to pass through said open jaws.

20. A surgical procedure for operating on tissue of a patient at a surgical site, comprising:
 a) delivering a first treatment apparatus having a pair of jaws which can be opened and closed to the surgical site;
 b) delivering a grasper to the surgical site;
 c) opening the pair of jaws;
 d) extending the grasper through a space between the open jaws;
 e) grasping the tissue with the grasper;
 f) locating the grasper with the tissue into the space between the open jaws; and
 g) closing the jaws onto the tissue, wherein
  said step of extending the grasper comprises moving the grasper distally through an opening in one of the jaws.

21. A surgical procedure according to claim 20, further comprising:
 h) applying a cauterizing energy to the tissue via the jaws.

22. A surgical procedure according to claim 21, wherein:
 said step of applying a cauterizing energy comprises providing a bipolar cautery current to the tissue.

23. A surgical procedure according to claim 22, wherein:
 said providing a bipolar cautery current comprises providing a bipolar cautery current with one of said pair of jaws coupled to a first pole, and a second of said pair of jaws coupled to a second pole.

24. A surgical procedure according to claim 22, wherein:
 said providing a bipolar cautery current comprises providing a bipolar cautery current with said grasper coupled to a first pole, and one or both of said pair of jaws coupled to a second pole.

25. A surgical procedure according to claim 20, wherein:
 said step of delivering a first treatment apparatus includes coupling the pair of jaws to the distal end of an endoscope without passing through any of the lumina of the endoscope.

26. A surgical procedure according to claim 25, wherein:
 said step of delivering a grasper to the surgical site includes delivering a grasper through a lumen of the endoscope.

27. A surgical system for use with an endoscope having a lumen, comprising:
 a) a first cautery treatment member;
 b) coupling means for coupling said first cautery treatment member to the distal end of the endoscope without passing through the endoscope;
 c) a second cautery treatment member extending through the lumen of the endoscope, said second cautery treatment member including an actuatable grasper; and
 d) cautery coupling means for coupling said first cautery treatment member to a first pole of cauterizing energy and said second cautery treatment member to a second pole of cauterizing energy.

* * * * *